(12) United States Patent
Kohama (10) Patent No.: US 11,969,525 B2
(45) Date of Patent: Apr. 30, 2024

(54) METHOD FOR PRODUCING MEDICAL INSTRUMENT

(71) Applicant: TERUMO KABUSHIKI KAISHA, Tokyo (JP)

(72) Inventor: Hiromasa Kohama, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 879 days.

(21) Appl. No.: 16/808,777

(22) Filed: Mar. 4, 2020

(65) Prior Publication Data

US 2020/0197576 A1 Jun. 25, 2020

Related U.S. Application Data

(63) Continuation of application No. PCT/JP2018/034070, filed on Sep. 13, 2018.

(30) Foreign Application Priority Data

Sep. 20, 2017 (JP) .................. 2017-180692
Jun. 12, 2018 (JP) .................. 2018-111807

(51) Int. Cl.
*A61L 29/08* (2006.01)
*A61L 29/14* (2006.01)
(Continued)

(52) U.S. Cl.
CPC .............. *A61L 29/085* (2013.01); *A61L 29/14* (2013.01); *A61L 31/10* (2013.01); *A61L 31/14* (2013.01);
(Continued)

(58) Field of Classification Search
CPC ..................... C08K 3/34; C08K 5/16
See application file for complete search history.

(56) References Cited

U.S. PATENT DOCUMENTS 5,218,018 A 6/1993 Tominaga et al.
5,670,558 A 9/1997 Onishi et al.
(Continued)

FOREIGN PATENT DOCUMENTS

CN 105073155 A 11/2015
CN 106999636 A 8/2017
(Continued)

OTHER PUBLICATIONS

The extended European Search Report dated Oct. 28, 2020, by the European Patent Office in corresponding European Patent Application No. 18858334.8-1109. (48 pages).
(Continued)

*Primary Examiner* — Dah-Wei D. Yuan
*Assistant Examiner* — Andrew J Bowman
(74) *Attorney, Agent, or Firm* — BUCHANAN INGERSOLL & ROONEY PC (57) ABSTRACT

Disclosed is a method for producing a medical instrument having a lubricating layer (a coating layer) exhibiting excellent durability (particularly, sliding durability). The method for producing a medical instrument is a method for producing a medical instrument having a base layer, and a lubricating layer that is carried on at least a part of the base layer. The method for producing a medical instrument also includes applying, to the base layer, a solution containing a block copolymer having a structural unit (A) derived from a reactive monomer having an epoxy group and a structural unit (B) derived from a hydrophilic monomer, an alkylammonium salt having 8 to 24 carbon atoms, and a solvent; and washing off the solution applied to the base layer.

20 Claims, 1 Drawing Sheet (51) Int. Cl.
*A61L 31/10* (2006.01)
*A61L 31/14* (2006.01)
*A61M 25/00* (2006.01)
*A61M 25/09* (2006.01)

(52) U.S. Cl.
CPC ........ *A61M 25/0009* (2013.01); *A61M 25/09* (2013.01); *A61L 2400/10* (2013.01); *A61L 2420/02* (2013.01); *A61L 2420/06* (2013.01); *A61M 2025/09108* (2013.01)

(56) References Cited

U.S. PATENT DOCUMENTS

| 5,939,208 | A | 8/1999 | Stoy | |
|---|---|---|---|---|
| 2004/0198882 | A1* | 10/2004 | Fujita | C08K 3/34 524/492 |
| 2011/0274917 | A1* | 11/2011 | Omata | A61L 29/14 428/704 |
| 2016/0015869 | A1 | 1/2016 | Omata et al. | |
| 2016/0175492 | A1 | 6/2016 | Kohama et al. | |
| 2017/0258966 | A1 | 9/2017 | Kohama et al. | |

FOREIGN PATENT DOCUMENTS

| EP | 0 435 356 A1 | 7/1991 | |
|---|---|---|---|
| EP | 0 693 293 A1 | 1/1996 | |
| EP | 2088173 | * 8/2009 | ............ C08L 101/10 |
| JP | H01292025 A | 11/1989 | |
| JP | H0415278 A | 1/1992 | |
| JP | H07233233 A | 9/1995 | |
| JP | H0833704 A | 2/1996 | |
| JP | 2012161372 A | 8/2012 | |
| WO | 2013/105394 A1 | 7/2013 | |

OTHER PUBLICATIONS

International Search Report (PCT/ISA/210) dated Nov. 27, 2018, by the Japanese Patent Office as the International Searching Authority for International Application No. PCT/JP2018/034070.

Written Opinion (PCT/ISA/237) dated Nov. 27, 2018, by the Japanese Patent Office as the International Searching Authority for International Application No. PCT/PCT/JP2018/034070.

Kubo, T., et al., "Antibacterial activities effectuated by co-continuous epoxy-based polymer materials", Colloids and Surfaces B: Biointerfaces, 2013 (month unknown), vol. 107, pp. 53.58.

Tanaka, Ryohei, "Epoxy resin", Colour Material, 1991 (month unknown), vol. 64, No. 10, pp. 655-665.

Office Action (The First Office Action) dated Jul. 30, 2021, by the State Intellectual Property Office of People's Republic of China in corresponding Chinese Patent Application No. 201880055951.5 and an English Translation of the Office Action. (13 pages).

* cited by examiner

METHOD FOR PRODUCING MEDICAL INSTRUMENT

CROSS-REFERENCES TO RELATED APPLICATIONS

This application is a continuation of International Application No. PCT/JP2018/034070 filed on Sep. 13, 2018, and claims priority to Japanese Application No. 2017-180692 filed on Sep. 20, 2017 and Japanese Application No. 2018-111807 filed on Jun. 12, 2018, the entire content of each of which is incorporated herein by reference.

FIELD OF THE INVENTION

The present invention generally relates to a method for producing a medical instrument.

BACKGROUND DISCUSSION

Medical instruments such as catheters and guide wires which are inserted into a living body are required to exhibit excellent lubricity to reduce damage of tissue such as blood vessels and to improve ease of use for operating medical personnel. For this reason, a method of coating a surface of a base layer of a medical instrument with a hydrophilic polymer having lubricity has been developed and put into practical use. Meanwhile, in order to maintain ease of use for operating medical personnel, it is also important that the hydrophilic polymer having lubricity can be maintained on the surface of the base layer when the operator uses the medical instrument. Accordingly, not only excellent lubricity but also durability against loads such as abrasion and scratch is required in coating with a hydrophilic polymer.

Japanese Patent Publication No. H08-33704 discloses an example of a medical instrument in which a water-soluble or water-swellable polymer is dissolved in a solvent in which a base of the medical instrument swells to produce a polymer solution, the base of the medical instrument is immersed in this polymer solution to swell, this polymer is cross-linked or polymerized on a surface of a base layer, and thereby a surface lubricating layer is formed on the surface of the base layer.

According to the technique disclosed in Japanese Patent Publication No. H08-33704, the surface lubricating layer exhibiting relatively favorable lubricity can be fixed to the base.

SUMMARY

Japanese Patent Publication No. H08-33704 discloses that it is preferable to use, as a water-soluble or water-swellable polymer, a block copolymer composed of a hydrophilic site exhibiting lubricity and a portion having an epoxy group. In a case where such a block copolymer is used, the epoxy group of the block copolymer can be cross-linked by a heating operation, and thereby the surface lubricating layer that is relatively difficult to peel off can be formed. However, favorable lubricity and excellent durability are in a trade-off relationship, and there is a need for a technique that enables compatibility of favorable lubricity and excellent durability.

In particular, medical instruments have been remarkably reduced in size and diameter in recent years, and medical techniques allowing medical instruments with higher flexibility to approach narrow lesion areas in a living body have been spreading. In addition, operation of medical instruments may continue for a long time in some cases in accordance with complication of medical procedures. Accordingly, there is a need for a technique that can further improve lubricity maintainability (e.g., durability) of a device surface as compared with the techniques of the related art in order to maintain favorable operability of devices even in the case of complicated lesion areas. More specifically, there is a demand for devices that can maintain high lubricity and have excellent sliding durability even in the case where sliding on a device surface is repeated.

Accordingly, there is a need for a technique that can improve durability, particularly, sliding durability, of medical instruments and can support medical procedures that are becoming more complicated and sophisticated.

Described herein are embodiments of a method for producing a medical instrument having a lubricating layer (a coating layer) exhibiting excellent durability (particularly, sliding durability).

Described herein are various embodiments of a method for producing a medical instrument having a lubricating layer coated onto a base layer of the medical instrument. An embodiment of the method described herein comprises applying, to a base layer, a solution further containing an alkylammonium salt having a specific carbon number in addition to a block copolymer having a reactive monomer having an epoxy group and a hydrophilic monomer, and by washing off the solution applied to the base layer.

An embodiment of the method described herein comprises applying, to the base layer, a solution containing a block copolymer having a structural unit (A) derived from a reactive monomer having an epoxy group and a structural unit (B) derived from a hydrophilic monomer, an alkylammonium salt having 8 to 24 carbon atoms, and a solvent; and washing off the solution applied to the base layer.

BRIEF DESCRIPTION OF THE DRAWINGS

In FIG. 1, 10 denotes a medical instrument; 1 denotes a base layer; and 2 denotes a lubricating layer.

In FIG. 2, 10 denotes a medical instrument; 1a denotes a core part of a base layer; 1b denotes a base surface layer; 1 denotes a base layer; and 2 denotes a lubricating layer.

DETAILED DESCRIPTION

Set forth below with reference to the accompanying drawings is a detailed description of embodiments of a method of coating a surface of a base layer of a medical instrument has been developed and put into practical use representing examples of the inventive method disclosed here. The dimensions or scales on the drawings may be exaggerated or different from actuality/reality for convenience of description and illustration. The following description does not limit the technical scope and terms used in the aspects.

Described herein is a method for producing a medical instrument having a base layer, and a lubricating layer that is carried on at least a part of the base layer, the method including: applying, to the base layer, a solution containing a block copolymer having a structural unit (A) derived from a reactive monomer having an epoxy group and a structural unit (B) derived from a hydrophilic monomer, an alkylammonium salt having 8 to 24 carbon atoms, and a solvent; and washing off the solution applied to the base layer. The method described herein produces a medical instrument having a lubricating layer exhibiting excellent durability, particularly, sliding durability.

In the below description, the structural unit (A) derived from a reactive monomer having an epoxy group is also simply referred to as a "structural unit derived from a reactive monomer" or a "structural unit (A)." Similarly, the structural unit (B) derived from a hydrophilic monomer is also simply referred to as a "structural unit derived from a hydrophilic monomer" or a "structural unit (B)." Furthermore, a block copolymer having a structural unit derived from a reactive monomer and a structural unit derived from a hydrophilic monomer is also simply referred to as a "block copolymer," and an alkylammonium salt having 8 to 24 carbon atoms is also simply referred to as an "alkylammonium salt."

In an embodiment of the method described herein, the solution containing the block copolymer having the structural unit derived from a reactive monomer and the structural unit derived from a hydrophilic monomer, the alkylammonium salt having a specific carbon number, and the solvent is applied to the base layer, and the solution applied to the base layer is washed off. In such an embodiment, the medical instrument thus produced exhibits excellent durability, e.g., surface lubricity maintainability and sliding durability. The mechanism by which a medical instrument obtained by the method described herein can exhibit excellent durability is described below. The method described herein is not limited to the embodiments described below.

In an embodiment, first, the block copolymer having the structural unit (A) derived from a reactive monomer having an epoxy group and the structural unit (B) derived from a hydrophilic monomer is applied to the base layer. Thereby, the lubricating layer is formed on the base layer. The block copolymer that forms the lubricating layer exhibits swelling properties when it comes into contact with body fluids and aqueous solvents, and thereby it imparts lubricity, e.g. surface lubricity, to medical instruments and reduces friction with luminal walls such as blood vessel walls.

The block copolymer forming the lubricating layer is applied as a solution, and is thereafter cross-linked or polymerized with the epoxy group contained in the structural unit (A) as a cross-linking point to form a network structure (or "network"). Additionally, the block copolymer is plasticized by addition of the alkylammonium salt having 8 to 24 carbon atoms and is polymerized by aggregation of blocks having similar properties, and thereby forms a network-like structure. The polymer is then cross-linked by a subsequent heat treatment and forms a network structure. The alkylammonium salt having 8 to 24 carbon atoms contained in the block copolymer solution promotes cross-linking or polymerization, including formation of a network by a plurality of cross-links or formation of a network by aggregation. Because a network structure in the lubricating layer can be formed at a higher density as a result, a firm coating layer (or the "lubricating layer") is formed, and the firm coating layer can be maintained favorably even after sliding. Thus, a high degree of lubricity, e.g. surface lubricity, can be maintained for a longer period of time while also improving sliding durability. Hereinafter, the cross-linking or polymerization of the block copolymer with the epoxy group contained in the block copolymer as a cross-linking point is also simply referred to as "cross-linking or polymerization of the block copolymer."

In addition, depending on the type of base layer (or "base"), a functional group on a surface of the base layer may react with and be bonded to the epoxy group contained in the structural unit (A). In this case, such a reaction is also promoted by the alkylammonium salt having 8 to 24 carbon atoms, the epoxy group is also bonded or fixed to the base layer, and thereby separation of the lubricating layer from the base layer can be suppressed and prevented.

Therefore, according to a method for producing a medical instrument described herein, a medical instrument having excellent durability, e.g. sliding durability, and surface lubricity maintainability can be obtained.

Hereinafter, embodiments of the method will be described. The method is not limited to only the following embodiments. In addition, dimensional ratios of the drawings are exaggerated for convenience of explanation and may differ from actual ratios in some cases.

In addition, as used herein, "X to Y" indicating a range includes X and Y, and means "X or more and Y or less." Furthermore, unless otherwise specified, operations, and measurements of physical properties or the like are performed under conditions of room temperature (20° C. to 25° C.)/relative humidity of 40% RH to 50% RH.

In an embodiment, the method for producing a medical instrument includes a solution application step (I) of applying, to the base layer, a solution containing a block copolymer having a structural unit (A) derived from a reactive monomer having an epoxy group and a structural unit (B) derived from a hydrophilic monomer, an alkylammonium salt having 8 to 24 carbon atoms, and a solvent; and a washing step (II) of washing off the solution applied to the base layer.

In other embodiments, the method further comprises a drying and/or heat treatment step (I') which may be performed between the solution application step (I) and washing step (II). A medical instrument having a lubricating layer exhibiting excellent durability can be obtained by applying a solution containing a specific alkylammonium salt and containing the block copolymer as described above.

Solution Application Step (I)

In an embodiment of the method for producing a medical instrument, first, the solution containing the block copolymer, the alkylammonium salt, and a solvent (hereinafter, also simply referred to a "block copolymer solution" or a "coating solution") is applied to the base layer in a (solution application step (I) (application layer forming step)). The solution application step (I) is performed for the purpose of carrying or coating the lubricating layer containing the block copolymer on at least a part of the surface of the base layer. The term "carrying" means a state in which the lubricating layer is fixed to the surface of the base layer in a state in which the lubricating layer is not easily separated therefrom, and indicates not only a form in which the entire surfaces of the base layer is completely covered by the lubricating layer, but also a form in which only a part of the base surface is covered by the lubricating layer, that is, a form in which the lubricating layer is attached to only a part of the surface of the base layer.

Accordingly, a method of applying the solution is not particularly limited except for using the solution containing the block copolymer having the structural unit (A) and the structural unit (B), the alkylammonium salt, and the solvent, and the method can be applied in the same manner as a known method or by appropriately modifying the known method.

In the solution application step (I), specifically, the coating solution is prepared by dissolving the block copolymer and the alkylammonium salt in a solvent, and an application layer is formed by coating the base with the coating solution.

Hereinafter, a preferred embodiment of the solution application step (I) will be described in detail.

Preparation of Block Copolymer Solution (Coating Solution)

As described above, in the solution application step (I), because the solution containing the block copolymer, the alkylammonium salt, and a solvent is applied to the base layer, the block copolymer solution (coating solution) is prepared first.

Block Copolymer

The block copolymer forms the lubricating layer carried on at least a part of the base layer. That is, in an embodiment, the lubricating layer contains the block copolymer in the medical instrument obtained by the method described herein.

The block copolymer has a structural unit (A) derived from a reactive monomer having an epoxy group and a structural unit (B) derived from a hydrophilic monomer.

The reactive monomer having an epoxy group constituting the block copolymer has an epoxy group as a reactive group. By introducing the structural unit (A) derived from such a reactive monomer into the block copolymer, the block copolymer is cross-linked or polymerized via the epoxy group, and thereby forms a network structure. As described above, since the addition of the alkylammonium salt promotes cross-linking or polymerization of the block copolymer, hardness of the lubricating layer can be improved. It is understood that the alkylammonium salt contributes to polymerization of the block copolymer by not only promoting cross-linking of epoxy groups, but also plasticizing the block copolymer and promoting aggregation of blocks having similar properties. Accordingly, the medical instrument obtained has excellent sliding durability and can maintain its shape favorably after sliding. In addition, depending on the type of base layer, the lubricating layer can be firmly bonded or fixed to the base layer via epoxy groups, and thereby separation of the lubricating layer from the base layer can be suppressed and prevented. Therefore, sliding durability of the medical instrument obtained is further improved.

The formation of the network structure by the structural units (A) constituting the block copolymer can be checked (confirmed) by a known method. In an aspect, the formation of the network structure may be checked (confirmed) by disappearance of epoxy groups and formation of ether bonds by ATR-IR. As specific ATR-IR measurement conditions, conditions described in the below Examples can be adopted.

The reactive monomer constituting the block copolymer is not particularly limited as long as it has an epoxy group, and known compounds can be used. Among them, the reactive monomer having an epoxy group preferably contains at least one selected from the group consisting of glycidyl acrylate, glycidyl methacrylate (GMA), 3,4-epoxycyclohexylmethyl acrylate, 3,4-epoxycyclohexylmethyl methacrylate, β-methylglycidyl methacrylate, and allyl glycidyl ether, because it is easy to control cross-linking or polymerization of the block copolymer. Among them, glycidyl (meth)acrylate is preferable in consideration of improvement of easy formation of the network structure, and ease of production. As used herein, "(meth)acrylate" includes both acrylate and methacrylate.

For the above reactive monomer, one kind may be used alone or two or more kinds may be used in combination. That is, a reactive site derived from the reactive monomer may be a homopolymer type composed of one type of reactive monomer alone, or may be a copolymer type composed of two or more types of reactive monomer. A form of the reactive site in a case where two or more types of reactive monomer are used may be a block copolymer or a random copolymer.

The hydrophilic monomer constituting the block copolymer has swelling properties upon contact with a body fluid or an aqueous solvent, and thereby imparts lubricity, e.g. surface lubricity, to a medical instrument. Accordingly, by introducing the structural unit (B) derived from such a hydrophilic monomer into the block copolymer, lubricity, e.g. surface lubricity, of the medical instrument is improved, and friction generated when the medical instrument comes into contact with luminal walls such as blood vessel walls can be reduced.

The hydrophilic monomer constituting the block copolymer is not particularly limited as long as it has above-mentioned characteristics, and known compounds can be used. Examples thereof include acrylamide and its derivatives, vinylpyrrolidone, acrylic acid and methacrylic acid and their derivatives, polyethylene glycol acrylate and its derivatives, monomers having sugars and phospholipids in their side chains, water-soluble monomers such as maleic anhydride, and the like. More specific examples thereof include acrylic acid, methacrylic acid, N-methylacrylamide, N,N-dimethylacrylamide (DMAA), acrylamide, acryloylmorpholine, N,N-dimethylaminoethyl acrylate, N-vinylpyrrolidone, 2-methacryloyloxyethyl phosphorylcholine, 2-methacryloyloxyethyl-D-glycoside, 2-methacryloyloxyethyl-D-mannoside, vinyl methyl ether, 2-hydroxyethyl (meth)acrylate, 4-hydroxybutyl (meth)acrylate, 2-hydroxypropyl (meth)acrylate, 2-hydroxybutyl (meth)acrylate, 6-hydroxyhexyl (meth)acrylate, 1,4-cyclohexanedimethanol mono(meth)acrylate, 1-chloro-2-hydroxypropyl (meth)acrylate, diethylene glycol mono(meth)acrylate, 1,6-hexanediol mono(meth)acrylate, pentaerythritol tri(meth)acrylate, dipentaerythritol penta(meth)acrylate, neopentyl glycol mono(meth)acrylate, trimethylolpropane di(meth)acrylate, trimethylolethane di(meth)acrylate, 2-hydroxy-3-phenyloxypropyl (meth)acrylate, 4-hydroxycyclohexyl (meth)acrylate, 2-hydroxy-3-phenyloxy (meth)acrylate, 4-hydroxycyclohexyl (meth)acrylate, cyclohexanedimethanol mono(meth)acrylate, poly(ethylene glycol)methyl ether acrylate, and poly(ethylene glycol)methyl ether methacrylate. The hydrophilic monomer preferably contains at least one selected from the group consisting of N,N-dimethylacrylamide, acrylamide, 2-hydroxyethyl methacrylate, and N-vinylpyrrolidone as use thereof imparts excellent lubricity, ease of synthesis, and operability. Among them, N,N-dimethylacrylamide is preferred as the hydrophilic monomer from the viewpoint of excellent lubricity.

For the hydrophilic monomer, one kind may be used alone or two or more kinds may be used in combination. That is, a hydrophilic site derived from the hydrophilic monomer may be a homopolymer type composed of one type of hydrophilic monomer alone, or may be a copolymer type composed of two or more types of hydrophilic monomer. A form of the hydrophilic site in a case where two or more types of hydrophilic monomer are used may be a block copolymer or a random copolymer.

The block copolymer has the structural unit (A) and the structural unit (B). A ratio of the structural unit (A) to the structural unit (B) is not particularly limited as long as the above-described effect is obtained. The molar ratio of the structural unit (A) to the structural unit (B) is preferably 1:2 to 1:100, more preferably 1:2 to 1:50, even more preferably 1:5 to 1:50, and particularly preferably 1:10 to 1:30, in consideration of favorable lubricity, lubricity maintainability, hardness of a coating layer, bonding properties with the base layer, and the like. When the ratio is within such a range, the structural unit (B) enables the lubricating layer to sufficiently exhibit lubricity, and the structural unit (A) enables the lubricating layer to exhibit sufficient hardness of a coating layer, bonding properties to the base layer, and durability. A molar ratio of the structural unit (A) to the structural unit (B) can be controlled by adjusting a molar ratio of each monomer in a step of producing the block copolymer. At this time, a molar ratio of the reactive monomer having an epoxy group and the hydrophilic monomer in the step of producing the block copolymer is preferably 1:2 to 1:100, and is more preferably 1:2 to 1:50, is even more preferably 1:5 to 1:50, and particularly preferably 1:10 to 1:30. The molar ratio of the structural unit (A) to the structural unit (B) can be checked (confirmed) by, for example, performing NMR measurement ($^1$H-NMR measurement, $^{13}$C-NMR measurement, or the like) on the copolymer.

A weight-average molecular weight of the block copolymer is preferably 10,000 to 10,000,000 from the viewpoint of solubility. The weight-average molecular weight of the block copolymer is more preferably 100,000 to 10,000,000 from the viewpoint of easy preparation of the block copolymer solution (coating solution). For the "weight-average molecular weight," values measured by gel permeation chromatography (GPC) using polystyrene as a standard substance are adopted.

In addition, a method for producing the block copolymer is not particularly limited, and for example, the block copolymer can be produced by applying known polymerization methods of the related art, such as a living radical polymerization method, a polymerization method using a macroinitiator, or a polycondensation method. Among them, the living radical polymerization method or the polymerization method using a macroinitiator is preferably used from the viewpoint that it is easy to control a molecular weight and molecular weight distribution of the structural unit (site) derived from the reactive monomer and the structural unit (site) derived from the hydrophilic monomer. The living radical polymerization method is not particularly limited, and for example, methods described in Japanese Patent Publication No. H11-263819, Japanese Patent Publication No. 2002-145971, Japanese Patent Publication No. 2006-316169, and the like; atom transfer radical polymerization (ATRP) method; and the like can be applied in the same manner or with appropriate modification. In addition, in the polymerization method using a macroinitiator, for example, a reactive site having a reactive functional group, and a macroinitiator having a radically polymerizable group such as peroxide groups are produced, and thereafter, the macroinitiator and a monomer for forming a hydrophilic site are polymerized, and thereby a block copolymer having a hydrophilic site and a reactive site can be produced.

In the polymerization of the block copolymer, it is possible to use known methods such as bulk polymerization, suspension polymerization, emulsion polymerization, solution polymerization, and the like. Specifically, in the production of the block copolymer, it is possible to use a method in which a reactive monomer and a hydrophilic monomer are copolymerized by stirring and heating them together with a polymerization initiator in a polymerization solvent. The polymerization initiator is not particularly limited and a known initiator may be used. In addition, the polymerization solvent is not particularly restricted, and for example, it is possible to use aliphatic organic solvents such as n-hexane, n-heptane, n-octane, n-decane, cyclohexane, methylcyclohexane, and liquid paraffin; ether solvents such as tetrahydrofuran and dioxane; aromatic organic solvents such as benzene, toluene, and xylene; halogen organic solvents such as 1,2-dichloroethane and chlorobenzene; and polar aprotic organic solvents such as N,N-dimethylformamide and dimethylsulfoxide. For the solvents described above, one kind may be used alone or two or more kinds thereof may be mixed and used.

A concentration of the monomer in the polymerization solvent, that is, a total concentration of the hydrophilic monomer and the reactive monomer together, is preferably 5% to 90% by mass, more preferably 8% to 80% by mass, and particularly preferably 10% to 50% by mass.

In the above polymerization, polymerization conditions are not particularly limited as long as the above copolymerization proceeds. For example, a polymerization temperature is preferably 30° C. to 150° C., and more preferably from 40° C. to 100° C. In addition, a polymerization time is preferably 30 minutes to 30 hours, and more preferably 3 to 24 hours.

Furthermore, at the time of copolymerization, chain transfer agents, polymerization rate regulators, surfactants, water-soluble polymers, water-soluble inorganic compounds—such inorganic compounds include, for example, alkali metal salts, alkali metal hydroxides, polyvalent metal salts, and non-reducing alkali metal salt pH buffers—inorganic acids, inorganic acid salts, organic acids and organic acid salts, and other additives may be used as appropriate.

The block copolymer after copolymerization is preferably purified by a general purification method such as a re-precipitation method, a dialysis method, an ultrafiltration method, and an extraction method.

Alkylammonium Salt

In an embodiment, the alkylammonium salt promotes cross-linking or polymerization of the block copolymer. Thereby, a firm lubricating layer can be formed, and excellent durability, e.g. sliding durability, can be obtained.

Promotion of cross-linking or polymerization of the block copolymer as described above can also be induced by adding a strong acid. However, when the strong acid is added, the cross-linking or polymerization in the block copolymer solution ("coating solution") proceeds rapidly, and as a result, a viscosity of the coating solution increases, and it becomes difficult to apply the coating solution uniformly. On the other hand, because the alkylammonium salt gradually promotes cross-linking or polymerization of the block copolymer, it is possible to inhibit an increase in viscosity of the coating solution due to the cross-linking or polymerization of the block copolymer in the coating solution as described above. Accordingly, in an embodiment, the coating solution can be uniformly applied by using the alkylammonium salt. In addition, when a strong acid is used, it is necessary to separately prepare a solution of the block copolymer and a solution of the strong acid, and apply these in order because of the reason described above. However, since it is sufficient to apply a liquid containing both the block copolymer and the alkylammonium salt when forming the lubricating layer (application layer), there is an advantage that the lubricating layer (application layer) can be formed by one liquid.

The alkylammonium salt has 8 to 24 carbon atoms. The number of carbon atoms refers to a total number of carbon atoms contained in an alkylammonium cation. When the alkylammonium salt has less than 8 carbon atoms, the alkylammonium salt cannot be uniformly dissolved in the block copolymer solution (coating solution), and it is difficult to uniformly apply the solution to the base layer. Accordingly, sufficient lubricity cannot be obtained. In addition, when the alkylammonium salt has more than 24 carbon atoms, a uniform solution can be prepared, but affinity between the alkylammonium salt and the lubricating layer (block copolymer) is high, and it is difficult to remove the alkylammonium salt when the lubricating layer is washed. Accordingly, the alkylammonium salt remains on the lubricating layer, and sufficient lubricity (surface lubricity) cannot be obtained. The alkylammonium salt preferably has 12 to 24 carbon atoms, and more preferably 16 to 20 carbon atoms from the viewpoint of forming a lubricating layer having excellent durability (sliding durability).

The alkylammonium salt used is not particularly limited as long as its cation moiety has 8 to 24 carbon atoms and has at least one alkyl group, and any of primary to quaternary ammonium salts may be used. The alkylammonium salt is preferably a quaternary ammonium salt from the viewpoint of easy availability and easier control of cross-linking or polymerization of the block copolymer.

In addition, in the alkylammonium salt, a cation moiety of the alkylammonium salt may have a substituent other than alkyl groups as long as the number of carbon atoms satisfies the above range. Other substituents are not particularly limited, and examples thereof include an alkenyl group, an alkynyl group, an aryl group, an acyl group, an alkoxycarbonyl group, an alkoxy group, an aryloxy group, an aryloxycarbonyl group, an acyloxy group, and the like. However, a form in which a cation moiety of the alkylammonium salt does not have a substituent other than alkyl groups is preferable from the viewpoint of easy availability and easier control of cross-linking or polymerization of the block copolymer. That is, the alkylammonium salt is preferably a tetraalkylammonium salt.

The alkyl group contained in the ammonium salt is not particularly limited as long as it satisfies the above carbon number. In addition, when the alkylammonium salt has two or more alkyl groups, the alkyl groups may be the same as or different from each other.

The alkyl groups contained in the alkylammonium salt each independently preferably are a linear or branched alkyl group having 2 to 6 carbon atoms or a cyclic alkyl group having 3 to 6 carbon atoms, more preferably a linear or branched alkyl group having 2 to 6 carbon atoms, even more preferably a linear alkyl group having 2 to 6 carbon atoms, and most preferably a linear alkyl group having 4 to 5 carbon atoms, from the viewpoint of excellent solubility in the block copolymer solution and easy promotion of cross-linking or polymerization of the block copolymer.

Examples of alkyl groups include linear, branched, or cyclic alkyl groups such as an ethyl group, an n-propyl group, an isopropyl group, an n-butyl group, an isobutyl group, a sec-butyl group, a tert-butyl group, an n-pentyl group, an isopentyl group, a neopentyl group, an n-hexyl group and a cyclohexyl group. Among them, the alkyl groups in the alkylammonium salt are each independently preferably selected from the group consisting of an ethyl group, an n-propyl group, an n-butyl group, an n-pentyl group, and an n-hexyl group, and more preferably are an n-butyl group or an n-pentyl group, from the viewpoint of excellent solubility in the block copolymer solution, and easier control of cross-linking or polymerization of the block copolymer.

Two or more alkyl groups contained in the alkylammonium salt are preferably the same as each other from the viewpoint of easy availability of the alkylammonium salt and easier control of cross-linking or polymerization of the block copolymer.

In consideration of the preferable alkyl groups described above, the alkylammonium salts are preferably selected from the group consisting of tetraethylammonium salts, tetra-n-propylammonium salts, tetra-n-butylammonium salts, tetra-n-pentylammonium salts, and tetra-n-hexylammonium salts, and are more preferably tetra-n-butylammonium salts or tetra-n-pentylammonium salts.

Meanwhile, anions, e.g. counter anions, that form the alkylammonium salt are not particularly limited as long as they can form a salt with the above alkylammonium cation. Examples of such anions include halide ions such as a fluoride ion, a chloride ion, a bromide ion, and an iodide ion; a hydrogen sulfate ion ($HSO_4^-$); a sulfate ion ($SO_4^{2-}$); a nitrate ion ($NO_3^-$); a dihydrogen phosphate ion ($H_2PO_4^-$); a hydrogen phosphate ion ($HPO_4^{2-}$); a phosphate ion ($PO_4^{3-}$); a perchlorate ion ($ClO_4^-$); a hydroxide ion ($OH^-$); and carboxylate anions such as a citrate ion, an acetate ion, a malate ion, a fumarate ion, a lactate ion, a glutarate ion, and a maleate ion. The anion of the alkylammonium salt is preferably selected from the group consisting of a halide ion, a hydrogen sulfate ion, a perchlorate ion, and a hydroxide ion because of their excellent solubility in the block copolymer solution.

In addition, the anion of the alkylammonium salt is more preferably a halide ion. Durability of the lubricating layer is extremely improved by using an alkylammonium salt having such an anion. The reason is considered as follows. Because alkylammonium salts having a halide ion as an anion have relatively weak basicity or is neutral, for example, in a case where the structural unit (A) contains an epoxy group or a glycidyl ester group, hydrolysis of a cross-linked portion of the epoxy group or the glycidyl ester group contained in the block copolymer hardly occurs. Accordingly, a lubricating layer thus formed is less susceptible to such hydrolysis, and as a result, hardness of the lubricating layer is improved, and thereby it is possible to form the lubricating layer having excellent durability (e.g., sliding durability).

From the viewpoint of forming a lubricating layer having excellent durability, the anion of the alkylammonium salt is preferably selected from the group consisting of a chloride ion, a bromide ion, and an iodide ion, and is particularly preferably a chloride ion or a bromide ion. Since alkylammonium salts having chloride or bromide ions as an anion do not cause hydrolysis of the block copolymer because of their particularly weak basicity, and cross-linking of epoxy groups or aggregation of blocks having similar properties is promoted, it is possible to form a lubricating layer having excellent durability.

As described above, it is preferable that the alkylammonium salt suitably used have Formula (1):

In Formula (1), $R_1$ to $R_4$ each independently are an ethyl group, an n-propyl group, an n-butyl group, an n-pentyl group, or an n-hexyl group; and $X^-$ is a halide ion, a hydrogen sulfate ion, a perchlorate ion, or a hydroxide ion.

From the viewpoint of forming a lubricating layer having excellent durability (e.g., sliding durability), in Formula (1), it is more preferable that $R_1$ to $R_4$ represent an ethyl group, an n-propyl group, an n-butyl group, an n-pentyl group, or an n-hexyl group (where a plurality of $R_1$ to $R_4$ are the same substituents); and $X^-$ is a halide ion, a hydrogen sulfate ion, a perchlorate ion, or a hydroxide ion. In addition, from the same viewpoint, it is even more preferable that $R_1$ to $R_4$ represent an n-butyl group or an n-pentyl group (where a plurality of $R_1$ to $R_4$ are the same substituents), and $X^-$ is a halide ion in Formula (1); it is particularly preferable that $R_1$ to $R_4$ represent an n-butyl group or an n-pentyl group (where a plurality of $R_1$ to $R_4$ are the same substituents), and $X^-$ is a chloride ion, a bromide ion, or an iodide ion in Formula (1); and it is most preferable that $R_1$ to $R_4$ represent an n-butyl group or an n-pentyl group (where a plurality of $R_1$ to $R_4$ are the same substituents), and $X^-$ is a chloride ion or a bromide ion in Formula (1).

An alkylammonium salt described above may be used alone or a combination of two or more of the above alkylammonium salts may be used.

Solvent

For the purpose of uniformly carrying the block copolymer on the base layer, a uniform solution containing the block copolymer and the alkylammonium salt is prepared, and this solution (coating solution) is applied to the base layer.

The solvent used for dissolving the block copolymer and the alkylammonium salt is not particularly limited as long as it can dissolve the block copolymer and the alkylammonium salt. Specific examples thereof include water, alcohols such as methanol, ethanol, isopropanol, and ethylene glycol, ketones such as acetone, methyl ethyl ketone, and cyclohexanone, esters such as ethyl acetate, halides such as chloroform, olefins such as hexane, ethers such as tetrahydrofuran (THF) and butyl ether, aromatics such as benzene and toluene, amides such as N,N-dimethylformamide (DMF), sulfoxides such as dimethyl sulfoxide, and the like, but the examples are not limited thereto. These may be used alone or in combination of two or more kinds thereof. Among them, the solvent of the solution (coating solution) is preferably ketones such as acetone, and amides such as DMF, and is particularly preferably acetone and DMF, from the viewpoint that the block copolymer and the alkylammonium salt can be uniformly dissolved, and the solution can be uniformly applied.

Other Components

The block copolymer solution (coating solution) for forming the lubricating layer may contain other components in addition to the block copolymer, the alkylammonium salt, and the solvent. Other components are not particularly limited, and in a case where a medical instrument such as a catheter is intended to be inserted into a body cavity or lumen, examples thereof include pharmaceutical active ingredients (bioactive substances) such as anticancer drugs, immunosuppressants, antibiotics, antirheumatic drugs, antithrombotic drugs, HMG-CoA reductase inhibitors, ACE inhibitors, calcium antagonists, antihyperlipidemic agents, integrin inhibitors, antiallergic agents, antioxidants, GPIIb/IIIa antagonists, retinoids, flavonoids, carotenoids, lipid improvers, DNA synthesis inhibitors, tyrosine kinase inhibitors, antiplatelet drugs, vascular smooth muscle growth inhibitors, anti-inflammatory drugs, biological materials, interferons, and NO production promoting substances. An amount of the other components added is not particularly limited, and a commonly used amount is similarly applied. Ultimately, an amount of other components added is appropriately selected in consideration of severity of disease for which the component is applied, a weight of a patient, and the like.

Preparation of Block Copolymer Solution (Coating Solution)

The block copolymer solution (coating solution) is prepared using the block copolymer described above, alkylammonium salt, and solvent. The order of addition of the above components, and a method of addition are not particularly limited. The above components may be added all at once or separately in a stepwise or continuous manner. In addition, a mixing method is not particularly limited, and a known method can be used. As a method for preparing a block copolymer solution (coating solution), a method a block copolymer and an alkylammonium salt are sequentially added to a solvent, and are stirred in the solvent in which is preferable.

A concentration of the block copolymer in the block copolymer solution (coating solution) is not particularly limited. From the viewpoint of further improving coatability, lubricity, and durability of the lubricating layer, a concentration of the block copolymer in the solution (coating solution) is preferably 0.01% to 20% by mass, more preferably 0.05% to 15% by mass, and particularly preferably 1% to 10% by mass. When the concentration of the block copolymer is within the above range, the lubricating layer to be obtained can exhibit sufficient lubricity and durability. That is, according to a preferred embodiment, the solution (block copolymer solution, coating solution) contains 0.01% to 20% by mass (more preferably 0.05% to 15% by mass, particularly preferably 1% to 10% by mass) of the block copolymer. In addition, when the concentration of the block copolymer is within the above range, it is preferable from the viewpoint that a uniform lubricating layer having a desired thickness can be easily obtained by one coating, and a viscosity of the solution is within an appropriate range, and thereby operability (for example, ease of coating) and production efficiency are improved. However, even when the concentration deviates from the above range, the solution still can be sufficiently used as long as it does not affect the lubricity or durability achieved.

A concentration of the alkylammonium salt in the block copolymer solution (coating solution) is also not particularly limited. A concentration of the alkylammonium salt in the solution (coating solution) is preferably 0.01% to 20% by mass, more preferably 0.05% to 15% by mass, and particularly preferably 1% to 10% by mass from the viewpoint that the cross-linking or polymerization of the block copolymer sufficiently proceeds, but does not proceed excessively (to the extent where cross-linking or polymerization can be appropriately promoted). When the concentration of the alkylammonium salt is within the above range, a lubricating layer to be obtained can exhibit sufficient lubricity and durability. However, even when the concentration deviates from the above range, the solution still can be sufficiently used as long as it does not affect the lubricity or durability achieved.

In addition, a mixing ratio of the block copolymer and the alkylammonium salt in the block copolymer solution (coating solution) is not particularly limited. The solution (coating solution) preferably contains the block copolymer and the alkylammonium salt at a mass ratio of 1:0.01 to 1:10, more preferably contains the block copolymer and the alkylammonium salt at a mass ratio of 1:0.05 to 1:5, particularly preferably contains the block copolymer and the alkylammonium salt at a mass ratio of 1:0.05 to 1:2, and particularly preferably contains the block copolymer and the alkylammonium salt at a mass ratio of 1:0.1 to 1:2, from the viewpoint of further improving coatability, lubricity, and durability of the lubricating layer. When the mass ratio of block copolymer and the alkylammonium salt is within the above range, a lubricating layer to be obtained can exhibit sufficient lubricity and durability. Lubricity of the lubricating layer is also improved because the alkylammonium salt can be sufficiently removed in a washing step to be described later.

Application of Block Copolymer Solution (Coating Solution)

Next, as described above, the solution (coating solution) containing the block copolymer, the alkylammonium salt, and the solvent is prepared, and then the solution is applied to the base layer.

The base layer may be made of any material, and examples thereof include a metal material, a polymer material (resin material), ceramics, and the like.

Among the materials constituting the base layer, the metal material is not particularly limited, and metal materials generally used for medical instruments such as a catheter, a guide wire, and an indwelling needle is used. Specific examples thereof include various stainless steels such as SUS304, SUS314, SUS316, SUS316L, SUS420J2, and SUS630, gold, platinum, silver, copper, nickel, cobalt, titanium, iron, aluminum, tin, various alloys such a nickel-titanium alloy, a nickel-cobalt alloy, a cobalt-chromium alloy, a zinc-tungsten alloy, and the like. These may be used alone or in combination of two or more kinds thereof. As the metal material described above, a metal material optimum for the base layer such as catheters, guide wires, and indwelling needles which are use applications may be appropriately selected.

In addition, among the materials constituting the base layer, the polymer material (resin material or elastomer material) is not particularly limited, and polymer materials generally used for medical instruments such as catheters, introducers, guide wires, and indwelling needles are used. Specific examples thereof include polyamide resin, polyolefin resin such as polyethylene resin and polypropylene resin, modified polyolefin resin, cyclic polyolefin resin, epoxy resin, polyurethane resin, diallyl phthalate resin (allyl resin), polycarbonate resin, fluorine resin, amino resin (urea resin, melamine resin, benzoguanamine resin), polyester resin such as polyethylene terephthalate resin and polybutylene terephthalate resin, styrene resin, acrylic resin, polyacetal resin, vinyl acetate resin, phenol resin, vinyl chloride resin, silicone resin (silicon resin), polyether resin, polyimide resin, and the like.

In addition, thermoplastic elastomers such as polyurethane elastomers, polyester elastomers, and polyamide elastomers can also be used as the material of the base layer.

These polymer materials may be used alone, or as a mixture of two or more kinds thereof, or as a copolymer of two or more kinds of monomers constituting any of the above resins or elastomers. Among them, as the polymer material, a polyethylene resin, a polyurethane resin, a polyethylene terephthalate resin, a polyamide resin, and a polyamide elastomer are preferable, and a polyamide resin and a polyamide elastomer are more preferable. A carboxy group or an amino group as a terminal group contained in a polyamide resin or a polyamide elastomer can undergo a cross-linking reaction with an epoxy group in the block copolymer. In addition, it can be said that these polymer materials (particularly, polyamide resins and polyamide elastomers) are relatively soft, and the block copolymer constituting the lubricating layer easily permeates therein. Accordingly, bonding properties between the polymer material (particularly, a polyamide resin and a polyamide elastomer) and the block copolymer are enhanced, and thereby it is possible to form a lubricating layer having excellent durability. As the polymer material described above, a polymer material optimum for the base layer such as catheters, guide wires, and indwelling needles which are use applications may be appropriately selected.

As will be described later, according to the method for producing a medical instrument described herein, even in a case where a temperature is maintained at a relatively low temperature after the block copolymer solution (coating solution) is applied, cross-linking or polymerization of the block copolymer progresses, and thereby a lubricating layer having excellent durability can be formed. In other words, an effect that enables lowering a temperature at which the lubricating layer is fixed to the base layer is also exhibited. Accordingly, in the method for producing a medical instrument described herein, a polymer material (a resin material or an elastomer material) is suitably used as a constituent material of the base layer. Since the lubricating layer can be fixed at a low temperature, even if the base layer contains a polymer material that is easily deformed or plasticized by heat, deformation and plasticization of the base layer are inhibited, and thereby dimensional stability is improved.

In addition, a shape of the base layer is not particularly limited, and is appropriately selected depending on use aspects, such as a sheet shape, a linear shape (e.g., a wire), and a tubular shape.

A method of applying (coating) the block copolymer solution (coating solution) to the surface of the base layer is not particularly limited, and it is possible to adopt known methods of the related art such as a coating and printing method, an immersion method (a dipping method, a dip coating method), a spraying method (a spray method), a spin coating method, a mixed-solution-impregnated sponge coating method, a bar coating method, a die coating method, a reverse coating method, a comma coating method, a gravure coating method, and a doctor knife method. Among them, it is preferable to use the immersion method (a dipping method, a dip coating method).

In a case where a lubricating layer is formed on a thin and narrow inner surface, such as catheters, guide wires, or injection needles, the base layer may be immersed in a coating solution so that the inside of the system is depressurized for defoaming. By defoaming under reduced pressure, the solution can be rapidly penetrated into the thin and narrow inner surface, thereby promoting formation of a lubricating layer.

In addition, in a case where a lubricating layer is formed only on a part of the base layer, by coating a part of the base layer with the coating solution by immersing only the part of the base layer in the coating solution, a lubricating layer can be formed on a desired surface portion of the base layer.

In a case where it is difficult to immerse only a part of the base layer in the coating solution, after protecting (coating or the like) a surface portion of the base layer, on which a lubricating layer is not need to be formed in advance, with a removable (attachable) suitable member or material, the base layer is immersed in the coating solution, and the base layer is coated with the coating solution. Thereafter, the protective member (material) on the surface portion of the base layer, on which a lubricating layer does not need to be formed, is removed. Thereafter, a reaction is caused by heat treatment or the like, and thereby, a lubricating layer can be formed on a desired surface portion of the base layer. However, the method for producing a medical instrument described herein is not limited to these forming methods, and a lubricating layer can be formed by appropriately using known methods of the related art. For example, in a case where it is difficult to immerse only a part of the base layer in the coating solution, other coating methods (for example, a method in which a coating solution is applied to a predetermined surface portion of a medical instrument using a spray device, a bar coater, a die coater, a reverse coater, a comma coater, a gravure coater, a spray coater, a doctor knife, or the like) may be adopted instead of the immersion method. In a case where both an outer surface and an inner surface of a cylindrical instrument need to have a lubricating layer due to the structure of the medical instrument, the immersion method (dipping method) is preferably used from the viewpoint that both the outer surface and the inner surface can be coated at one time.

A coating amount of the block copolymer solution (coating solution) is preferably an amount at which a thickness of a film thus obtained (a lubricating layer) becomes 0.1 to 10 µm, is more preferably an amount at which a thickness of a film thus obtained (a lubricating layer) becomes 0.5 to 5 µm, and is even more preferably an amount at which a thickness of a film thus obtained (a lubricating layer) becomes 1 to 3 µm. When the coating amount is an amount at which a thickness of a coating (lubricating layer) becomes 0.1 µm or more, durability of the obtained coating (lubricating layer) can be sufficiently achieved. In addition, when the coating amount is an amount at which a thickness of a coating (lubricating layer) becomes 10 µm or less, a surface of the coating (lubricating layer) becomes less sticky, and therefore handling during production becomes easier.

Drying and/or Heat Treatment Step (I')

In an embodiment of the method for producing a medical instrument described herein, a drying and/or heat treatment step is preferably performed after the block copolymer solution (coating solution) is applied to the base layer to form an application layer, for the purpose of removing a solvent or forming a firm lubricating layer.

Hereinafter, a preferred embodiments of a drying and/or heat treatment step (I') for the block copolymer solution (coating solution) will be described in detail.

In the solution application step (I), it is preferable to apply the solution (coating solution) containing the block copolymer and the alkylammonium salt to the base layer, and then perform drying and/or heat treatment. The term "drying treatment" and "heat treatment" are not strictly distinguished, but for convenience of explanation, "drying treatment" in which the base layer to which the coating solution is applied is maintained at a temperature around room temperature or lower (20° C. to 30° C.) is referred to as the "drying treatment," and "heat treatment" in which the base layer is maintained at a temperature exceeding a temperature around room temperature (20° C. to 30° C.) is referred to as the "heat treatment."

Conditions for drying or heat treatment are not particularly limited as long as a lubricating layer containing the block copolymer can be formed on the base layer.

A temperature at the drying or heat treatment is not particularly limited, but is preferably 10° C. to 200° C. That is, after applying the block copolymer solution to the base layer (after forming an application layer), it is more preferable to maintain the application layer at 10° C. to 200° C. By maintaining the temperature at such a temperature, cross-linking or polymerization of the block copolymer is effectively promoted, and thereby a firm coating layer (lubricating layer) is formed. Accordingly, high lubricity (e.g., surface lubricity) can be maintained for a longer period. Furthermore, by maintaining the temperature at such a temperature, it is possible to inhibit the cross-linking or polymerization from excessively progressing. Therefore, it is possible to inhibit a deterioration in swelling properties caused by the lubricating layer becoming too hard, and as a result, favorable lubricity (e.g., surface lubricity) can be maintained.

In addition, after applying the block copolymer solution to the base layer (after forming the application layer), it is more preferable to maintain the application layer at 110° C. or lower, more preferably at 25° C. to 110° C., and most preferably at 50° C. to 100° C. By maintaining the temperature at such a temperature, excellent lubricity can be exhibited, and a lubricating layer having high durability can be formed. In particular, when the temperature is set to 110° C. or lower, excessive cross-linking or polymerization of the block copolymer can be inhibited even when the heat treatment is performed for a long time. Accordingly, a deterioration in swelling properties caused by the lubricating layer becoming too hard can be inhibited, and lubricity can be controlled more easily. The above temperature may be changed during drying or heat treatment.

In the production method described herein, one of the characteristics is that a lubricating layer having high durability can be formed even when the temperature is maintained at a relatively low temperature, for example, 80° C. or lower, or for example, 25° C. to 80° C. after the block copolymer solution (coating solution) is applied as described above. Accordingly, there is an advantage that even a polymer material which is easily deformed or plasticized by heat can be used as the base layer. Therefore, selectivity of materials is higher, and medical instruments for various use applications can be produced. In addition, since a lubricating layer having excellent durability can be formed at a low temperature, the method described herein is preferable also from the viewpoint of energy costs when producing medical instruments.

Furthermore, a time for the drying or heat treatment is not particularly limited, but it is preferably 30 minutes to 30 hours, more preferably 1 to 25 hours, and particularly preferably 1 to 10 hours. By setting the time as described above, cross-linking or polymerization in the block copolymer is effectively promoted, and thereby a firm coating layer (lubricating layer) is formed. Accordingly, high lubricity (surface lubricity) can be maintained for a longer period. Furthermore, by maintaining the time at such a time, it is possible to inhibit the cross-linking or polymerization from excessively progressing. Therefore, it is possible to inhibit a deterioration in swelling properties caused by the lubricating layer becoming too hard, and as a result, favorable lubricity (e.g., surface lubricity) can be maintained.

In the present step, it is preferable to further perform heat treatment after the drying treatment from the viewpoint of particularly effectively (efficiently) promoting the cross-linking or polymerization of the block copolymer. As described above, since heat treatment is further performed in a state where the solvent is distilled off by the drying and the heat treatment (that is, in a state where the block copolymer and the alkylammonium salt are easily brought into contact with each other), the effect of promoting cross-linking or polymerization of the block copolymer by the alkylammonium salts is further improved. Accordingly, even a polymer material which is easily deformed or plasticized by heat can be used as the base layer since the heat treatment can be performed in a shorter time.

Conditions (a temperature, a time, and the like) of the drying and heat treatment at this time are not particularly limited, but from the viewpoint of efficiently producing a medical instrument, it is preferable to perform the drying treatment of maintaining a temperature at 10° C. to 30° C. for 30 minutes to 5 hours, and then perform the heat treatment of maintaining a temperature at 40° C. to 200° C. for 1 to 10 hours. From the same viewpoint, it is more preferable to perform the drying treatment of maintaining a temperature at 20° C. to 30° C. for 30 minutes to 3 hours, and then perform the heat treatment of maintaining a temperature at 45° C. to 150° C. for 1 to 6 hours; and it is particularly preferable to perform the drying treatment of maintaining a temperature at 20° C. to 25° C. for 30 minutes to 1.5 hours, and then perform the heat treatment of maintaining a temperature at 50° C. to 100° C. for 2 to 6 hours. As described above, a medical instrument including a lubricating layer having excellent durability can be produced at a low temperature in a short time.

On the other hand, in a case where the alkylammonium salt contained in the block copolymer solution sufficiently promotes cross-linking or polymerization of the block copolymer, heat treatment is not required, and only drying treatment may be performed. At this time, conditions (a temperature, a time, and the like) of the drying treatment are not particularly limited, but from the viewpoint of forming a lubricating layer having excellent lubricity and high durability, a treatment temperature is preferably 10° C. to 30° C., and is more preferably 20° C. to 25° C. In addition, a treatment time is preferably 5 to 30 hours, more preferably from 10 to 25 hours.

Based on the above descriptions, in the drying and/or heat treatment, it is preferable to perform the drying treatment of maintaining a temperature at 20° C. to 25° C. for 30 minutes to 1.5 hours and then perform the heat treatment of maintaining a temperature at 50° C. to 100° C. for 2 to 6 hours; alternatively, it is preferable to perform the drying treatment of maintaining a temperature at 20° C. to 25° C. for 10 to 25 hours.

Under the above conditions (a temperature, a time, and the like), a firm lubricating layer (coating layer) can be carried on the surface of the base layer. In addition, depending on the type of base layer, a cross-linking reaction occurs via epoxy groups in the block copolymer in the lubricating layer, and thereby a highly firm lubricating layer that does not easily peel off from the base layer can be formed. Accordingly, peeling of the lubricating layer from the base layer can be effectively inhibited or prevented by the drying and/or heat treatment step.

In addition, pressure conditions during drying are not particularly limited, and the drying may be performed under normal pressure (atmospheric pressure), or may be performed under increased or reduced pressure.

It is possible to use, for example, an oven, a vacuum dryer, or the like can be used as drying or heating means or apparatus, but in the case of natural drying, the drying means or apparatus is not particularly required.

Washing Step (II)

In an embodiment of the method for producing a medical instrument described herein, after performing the solution application step (I) or the optional drying and/or heat treatment step (I'), the lubricating layer provided on the base layer is washed (washing step (II)). The washing step is performed for the purpose of removing the alkylammonium salts contained in the block copolymer solution (coating solution) and imparting excellent lubricity (i.e., low frictional properties) to the lubricating layer.

Hereinafter, a preferred embodiment of the washing step (II) will be described in detail.

A washing method is not particularly limited, but it may be a method of dipping a coating (lubricating layer) formed by the block copolymer in a washing solvent, a method of flowing a washing solvent, or a combination thereof. The washing solvent used at this time is not particularly limited as long as it does not dissolve the coating (lubricating layer) formed by the block copolymer and can remove impurities including the alkylammonium salts, but water or warm water is preferably used. A temperature of washing water is not particularly limited, but it is preferably 20° C. to 100° C., and more preferably 25° C. to 80° C. In addition, a washing time (a time for bringing a washing solvent into contact with a coating) is not particularly limited, but it is preferably 1 to 60 minutes, and more preferably 5 to 30 minutes. According to the above conditions, the alkylammonium salts can be sufficiently removed. As a result, a lubricating layer formed on the base layer can exhibit excellent lubricity.

After the washing step, a drying step may be further performed. A drying method and drying conditions (e.g., a temperature, a time, and the like) are not particularly limited, and known methods of the related art can be used.

The medical instrument produced by the method described herein has a structure in which the lubricating layer is carried on the base layer by applying the solution (coating solution) containing the block copolymer that forms the lubricating layer and the alkylammonium salts to the base layer. At this time, in order to improve lubricity, an amount of the alkylammonium salts contained in the lubricating layer is preferably as small as possible, but alkylammonium salts may not be completely removed and may remain. In such a case, it is determined that the medical instrument was produced by the method described herein. Specifically, it is confirmed by detecting alkylammonium salts by the following analysis method.

On the other hand, in order to obtain a medical instrument having favorable lubricity, an amount of the alkylammonium salts contained in the lubricating layer after the washing step is preferably 50 μg/cm$^2$ or less, and more preferably 5 μg/cm$^2$ or less per unit area. When the amount is 50 μg/cm$^2$ or less, the lubricating layer can exhibit excellent lubricity. Meanwhile, the lower limit is not particularly limited and is preferably as small as possible, but it is 1 μg/cm$^2$ or more in consideration of substantial removal efficiency of the alkylammonium salts and practical lubricity of the lubricating layer.

A content of the alkylammonium salts "per unit area" means a content of alkylammonium salts contained per unit area (1 cm$^2$) of the lubricating layer, and refers to a value obtained by dividing a mass (μg) of the alkylammonium salts measured by the following method by an area (cm$^2$) of the lubricating layer.

Specifically, a lubricating layer (a medical instrument having a lubricating layer) is immersed in water and kept at 70° C. for 24 hours. Then, the obtained extract (water) is subjected to LC-MS measurement under the following conditions.

LC/MS Measurement Conditions

LC/MS system: Waters 2695/Quattro micro API (LC)

LC model: Waters 2695

Column: XBridge Amide manufactured by Waters, 2.1 mm×150 mm, 3.5 μm

Mobile phase: 20 mmol/L ammonium formate solution (pH 3.2)/acetonitrile (1:9 (volume ratio))

Flow rate: 0.2 mL/min

Column temperature: 40° C.

(MS)
MS model: Waters Quattro micro API
Ionization method: ESI-Positive

Medical Equipment

A medical instrument having the lubricating layer exhibiting excellent durability can be produced by performing the solution application step (I) (application layer forming step), the washing step (II), and if necessary, the drying and/or heat treatment step (I') as described above.

That is, according to a method described herein, a firm lubricating layer that is not easily separated from the base layer can be formed by forming an application layer containing the block copolymer and the alkylammonium salts on the surface of the base layer, and then cross-linking epoxy groups. In addition, the medical instrument obtained by a method described herein can exhibit excellent lubricity and lubricity maintainability because the lubricating layer formed by the block copolymer is formed on the surface of the medical instrument.

Hereinafter, a preferred embodiment of the medical instrument produced by a method described herein will be described with reference to the attached drawings.

Figure 1:
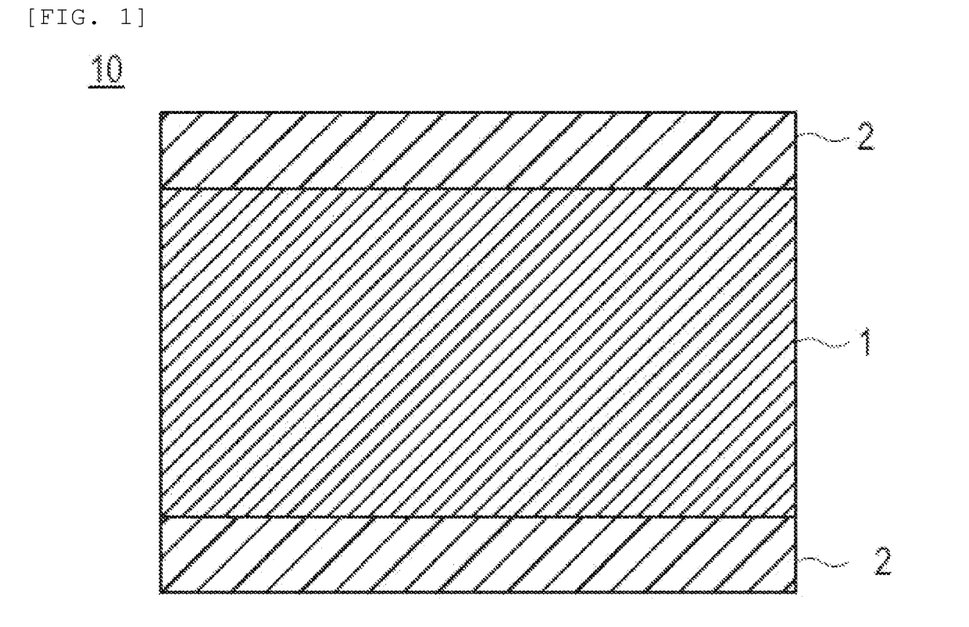
FIG. 1 is a partial cross-sectional view schematically showing a surface laminate structure of a representative embodiment of a medical instrument produced by a method described herein.
Figure 2:
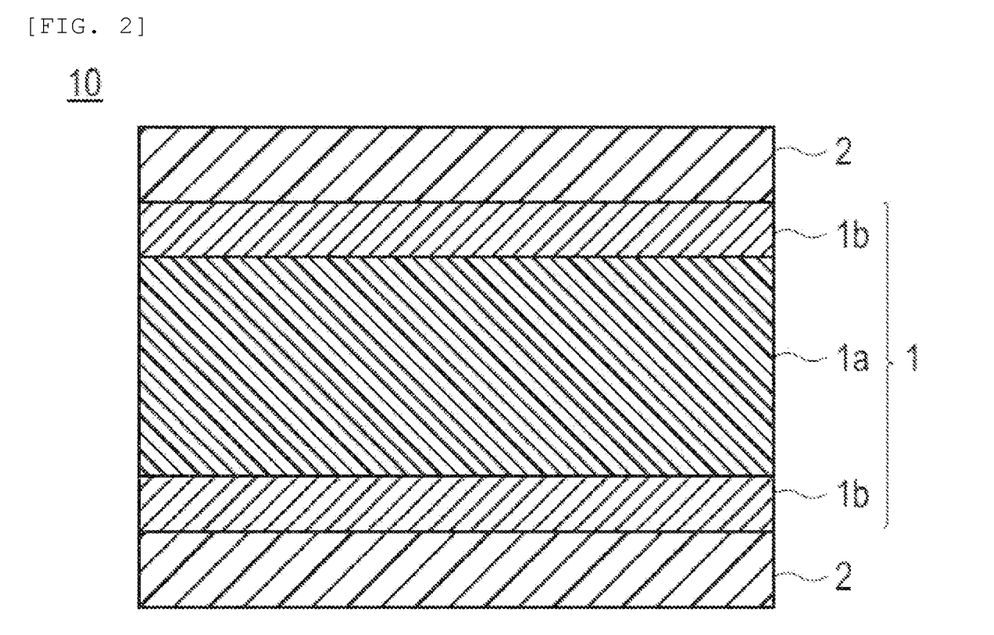
FIG. 2 is a partial cross-sectional view schematically showing a configuration example having a different surface laminate structure as an application example of the embodiment of FIG. 1.

FIG. 1 is a partial cross-sectional view schematically showing a surface laminate structure of a representative embodiment of a medical instrument (hereinafter abbreviated as a "medical instrument") produced by a method described herein. FIG. 2 is a partial cross-sectional view schematically showing a configuration example having a different surface laminate structure as an application example of the embodiment of FIG. 1. In addition, symbols in FIG. 1 and FIG. 2 are as follows: "1" denotes a base layer; "1a" denotes a core part of the base layer; "1b" denotes a base surface layer; "2" denotes a lubricating layer; and "10" denotes a medical instrument produce by the method described herein.

As shown in FIGS. 1 and 2, an embodiment of a medical instrument 10 includes the base layer 1, and the lubricating layer 2 that contains the block copolymer and that is provided on at least a part of the base layer 1 (the drawings show an example in which the lubricating layer is provided on the entire surface (both surfaces) of the base layer 1 in the drawing). In FIGS. 1 and 2, the lubricating layer 2 is formed on both surfaces of the base layer 1. However, the method described herein is not limited to the above-described embodiments, and may adopt any aspect such as an aspect in which the lubricating layer is formed on one surface of the base layer 1, and an aspect in which the lubricating layer is formed at a part of one or both surfaces of the base layer 1.

Hereinafter, each component of the medical instrument will be described in detail.

Base Layer (Base)

The base layer used in the present embodiment may be made of any material, and the material is not particularly limited. Specific examples of materials forming the base layer 1 include a metal material, a polymer material, ceramics, and the like. Specific examples of materials forming the base layer 1 are as described in the above section "Application of block copolymer solution (coating solution)"

The entire base layer 1 may be made of any of the above materials. The base layer 1 may have a multilayer structure in which different materials are stacked in multiple layers, or may have a structure in which members made of different materials are connected to each other for each part of the medical instrument. Alternatively, as shown in FIG. 2, the base layer 1 may have a structure in which the surface of the core part 1a of the base layer composed of any of the above-mentioned materials is coated with any of the above-mentioned materials by an appropriate method to form the base surface layer 1b. Examples of the latter case include a structure in which the surface of the core part 1a of the base layer formed of a resin material or the like is coated with a metal material by an appropriate method (known methods of the related art such as plating, metal deposition, or sputtering) to form the base surface layer 1b; a structure in which the surface of the core part 1a of the base layer formed of hard reinforcing materials such as metal materials or ceramic materials is coated with polymer materials that are more flexible than reinforcing materials such as metal materials by an appropriate method (known methods of the related art such as immersion (dipping), spraying (spraying), and application and print) to form the base surface layer 1b, or alternatively, a reinforcing material and a polymer material forming the core part 1a of the base layer are compounded to form the base surface layer 1b; and the like. In addition, the core part 1a of the base layer may have a multilayer structure in which different materials are stacked in multiple layers, or may have a structure in which members made of different materials are connected to each other for each part of the medical instrument. Furthermore, another middle layer (not shown) may be formed between the core part 1a of the base layer and the base surface layer 1b. Furthermore, the base surface layer 1b also may have a multilayer structure in which different materials are stacked in multiple layers, or may have a structure in which members made of different materials are connected to each other for each part of the medical instrument.

Lubricating Layer (Surface Lubricating Layer and Coating Layer)

The lubricating layer is carried on at least a part of the base layer 1. The reason why the lubricating layer 2 is carried on at least a part of the surface of the base layer 1 is because, in medical instruments such as catheters, guide wires, and indwelling needles which are use applications, it is sufficient for the lubricating layer be carried only on a surface portion where the surface is required to have lubricity when the lubricating layer is wet (a part of the surface or entire surface depending on cases), and not all surfaces (the entire surface) of these medical instruments are required to have lubricity when the lubricating layer is wet. Accordingly, in embodiments as described above, the lubricating layer may be formed to cover both surfaces of the base layer as shown in FIGS. 1 and 2; the lubricating layer may be formed to cover only one entire surface of the base layer; the lubricating layer may be formed to cover a part of both surfaces of the base layer by the same or different forms; the lubricating layer may be formed to cover a part of one surface of the base layer; and the like.

Use Applications of Medical Instrument

The medical instrument produced by the method described herein is a device used by coming into contact with a body fluid, blood, or the like, and has a lubricating surface in an aqueous liquid such as a body fluid or a physiological salt solution, and is capable of improving operability and reducing damage to the tissue mucosa. Specific examples thereof include catheters, guide wires, indwelling needles, and the like which are used in blood vessels, and other examples include the following medical instruments:

(a) Catheters that are orally or nasally inserted or indwelled in the digestive tract, such as gastric tube catheters, feeding catheters, and tubes for tubal feeding.

(b) Catheters that are orally or nasally inserted or indwelled in the respiratory tract or trachea, such as oxygen catheters, oxygen cannulas, tubes and cuffs for endotracheal tube, tubes and cuffs for tracheostomy tube, and endotracheal suction catheters.

(c) Catheters that are inserted or indwelled in the urethra or ureter, such as urethral catheters, urinary catheters, and catheters and balloons for urethral balloon catheters.

(d) Catheters that are inserted or indwelled in various lumens in a living body, organs, or tissues, such as suction catheters, drainage catheters, and rectal catheters.

(e) Catheters that are inserted or indwelled in blood vessels, such as indwelling needles, IVH catheters, thermodilution catheters, angiography catheters, vasodilation catheters, and dilators or introducers; or guide wires, stylets, and the like for these catheters.

(f) Artificial trachea, artificial bronchi, and the like.

(g) Medical instruments for extracorporeal circulation treatment (e.g., an artificial lung, artificial heart, artificial kidney, and the like) and their circuits.

EXAMPLES

The effects of the certain embodiments of the method described herein will be explained using the following examples and comparative examples. However, the technical scope of the method described herein is not only limited to the following examples. In the following examples, the operation was carried out at room temperature (25° C.) unless otherwise specified. In addition, unless otherwise specified, "%" and "part" respectively mean "% by mass" and "parts by mass."

Synthesis Example 1: Synthesis of Block Copolymer (1)

The following reaction was carried out to produce a block copolymer (1).

29.7 g of triethylene glycol was added dropwise into 72.3 g of adipic dichloride at 50° C., hydrochloric acid was removed under reduced pressure at 50° C. for 3 hours, and an oligoester was obtained. Next, 4.5 g of methyl ethyl ketone was added to 22.5 g of the obtained oligoester. The mixture was added dropwise to a solution containing 5 g of sodium hydroxide, 6.93 g of 31% hydrogen peroxide, 0.44 g of dioctyl phosphate as a surfactant, and 120 g of water, and was reacted at −5° C. for 20 minutes. The obtained product was repeatedly washed with water and methanol and then dried, and thereby a polyperoxide (PPO) having a plurality of peroxide groups in a molecule was obtained.

Next, 0.5 g of this PPO, 9.5 g of glycidyl methacrylate (GMA), and 30 g of benzene were used as a solvent, and polymerization was performed at 80° C. for 2 hours while stirring under reduced pressure. The reaction product obtained after the polymerization was reprecipitated with diethyl ether to obtain polyglycidyl methacrylate (PPO-GMA) having a plurality of peroxide groups in a molecule.

Subsequently, 1.0 g of the obtained PPO-GMA (equivalent to 7 mmol of GMA) was charged into 9.0 g of dimethylacrylamide (DMAA) and 90 g of dimethyl sulfoxide as a solvent, and the mixture was reacted at 80° C. for 18 hours. The reaction product obtained after the reaction was reprecipitated with hexane and recovered, and thereby a block copolymer (1) having an epoxy group in a molecule and exhibiting lubricity when wetted was obtained (structural unit (A):structural unit (B)=GMA:DMAA=1:14 (molar ratio)). When the block copolymer (1) thus obtained was analyzed by NMR and ATR-IR, it was checked (observed) that an epoxy group was present in the molecule. In addition, a weight-average molecular weight (Mw) of the block copolymer (1) measured by gel permeation chromatography (GPC, polystyrene conversion) was about 1.5 million.

Example 1

The block copolymer (1) obtained in Synthesis Example 1 was dissolved in N,N-dimethylformamide (DMF) such that a concentration became 6% by mass, and tetraethylammonium bromide (Tokyo Chemical Industry Co., Ltd.) was added by an amount (mass ratio) 0.5 times the amount of the block copolymer (1) and dissolved, and thereby a mixed solution was prepared. A tube made of a polyamide elastomer (VESTAMID (registered trademark) E62-S1 manufactured by Daicel-Evonik Ltd.) having an outer diameter of 5 Fr (1.65 mm diameter) was immersed in the above mixed solution, dried at room temperature (25° C.) for 1 hour to form a coating film. In addition, the tube was stored in an oven at 80° C. for 5 hours to heat the coating film. After cooling the coating film to room temperature, it was immersed in water at room temperature for 10 minutes, and thereby tetraethylammonium bromide was eluted and removed from the coating film. The tube was dried at room temperature to produce a coated tube (1) having a coating layer (lubricating layer) (a film thickness after drying=2 μm) containing a cross-linked copolymer derived from the block copolymer (1) on the surface.

A surface analysis of the coated tube (1) was performed by ATR-IR, a peak of the epoxy group became small, and the reaction of the epoxy group was checked (observed). In addition, no peak of tetraethylammonium bromide was checked (observed).

When the coated tube (1) was immersed in a physiological salt solution at 25° C. and rubbed with a finger, it was checked (observed) that a slippery and lower frictional surface was formed, as compared with an untreated tube.

Surface analysis by ATR-IR was performed under the following conditions (the same applies hereinafter).

ATR-IR Analysis Conditions

Equipment: Fourier transform infrared spectrophotometer Spectrum 100 manufactured by PerkinElmer Measurement mode: ATR method Detector: ZnSe Resolution: 4 $cm^{-1}$ Measuring range: 4000 to 650 $cm^{-1}$ Number of times of integration: 4 times Example 2

A coated tube (2) was produced in the same manner as in Example 1 except that tetrapropylammonium bromide (Tokyo Chemical Industry Co., Ltd.) was used instead of tetraethylammonium bromide.

A surface analysis of the coated tube (2) was performed by ATR-IR, a peak of the epoxy group became small, and the reaction of the epoxy group was checked (observed). In addition, no peak of tetrapropylammonium bromide was checked (observed).

When the coated tube (2) was immersed in a physiological salt solution at 25° C. and rubbed with a finger, it was checked (observed) that a slippery and lower frictional surface was formed, as compared with an untreated tube.

Example 3

A coated tube (3) was produced in the same manner as in Example 1 except that tetrabutylammonium bromide (Tokyo Chemical Industry Co., Ltd.) was used instead of tetraethylammonium bromide.

A surface analysis of the coated tube (3) was performed by ATR-IR, a peak of the epoxy group became small, and the reaction of the epoxy group was checked (observed). In addition, no peak of tetrabutylammonium bromide was checked (observed).

When the coated tube (3) was immersed in a physiological salt solution at 25° C. and rubbed with a finger, it was checked (observed) that a slippery and lower frictional surface was formed, as compared with an untreated tube.

Example 4

A coated tube (4) was produced in the same manner as in Example 1 except that tetrapentylammonium bromide (Tokyo Chemical Industry Co., Ltd.) was used instead of tetraethylammonium bromide.

A surface analysis of the coated tube (4) was performed by ATR-IR, a peak of the epoxy group became small, and the reaction of the epoxy group was checked (observed). In addition, no peak of tetrapentylammonium bromide was checked (observed).

When the coated tube (4) was immersed in a physiological salt solution at 25° C. and rubbed with a finger, it was checked (observed) that a slippery and lower frictional surface was formed, as compared with an untreated tube.

Example 5

A coated tube (5) was produced in the same manner as in Example 1 except that tetrahexylammonium bromide (Tokyo Chemical Industry Co., Ltd.) was used instead of tetraethylammonium bromide.

A surface analysis of the coated tube (5) was performed by ATR-IR, a peak of the epoxy group became small, and the reaction of the epoxy group was checked (observed). In addition, no peak of tetrahexylammonium bromide was checked (observed).

When the coated tube (5) was immersed in a physiological salt solution at 25° C. and rubbed with a finger, it was checked (observed) that a slippery and lower frictional surface was formed, as compared with an untreated tube.

Example 6

A coated tube (6) was produced in the same manner as in Example 1 except that tetrabutylammonium fluoride (Aldrich, a tetrahydrofuran solution) was used instead of tetraethylammonium bromide, and a tube made of polyethylene (NOVATEC (registered trademark) HB530 manufactured by Japan Polyethylene Corporation) was used instead of polyamide elastomer.

A surface analysis of the coated tube (6) was performed by ATR-IR, a peak of the epoxy group became small, and the reaction of the epoxy group was checked (observed). In addition, no peak of tetrabutylammonium fluoride was checked (observed).

When the coated tube (6) was immersed in a physiological salt solution at 25° C. and rubbed with a finger, it was checked (observed) that a slippery and lower frictional surface was formed, as compared with an untreated tube.

Example 7

A coated tube (7) was produced in the same manner as in Example 6 except that tetrabutylammonium chloride (Tokyo Chemical Industry Co., Ltd.) was used instead of tetrabutylammonium fluoride.

A surface analysis of the coated tube (7) was performed by ATR-IR, a peak of the epoxy group became small, and the reaction of the epoxy group was checked (observed). In addition, no peak of tetrabutylammonium chloride was checked (observed).

When the coated tube (7) was immersed in a physiological salt solution at 25° C. and rubbed with a finger, it was checked (observed) that a slippery and lower frictional surface was formed, as compared with an untreated tube.

Example 8

A coated tube (8) was produced in the same manner as in Example 6 except that tetrabutylammonium bromide (Tokyo Chemical Industry Co., Ltd.) was used instead of tetrabutylammonium fluoride.

A surface analysis of the coated tube (8) was performed by ATR-IR, a peak of the epoxy group became small, and the reaction of the epoxy group was checked (observed). In addition, no peak of tetrabutylammonium bromide was checked (observed).

When the coated tube (8) was immersed in a physiological salt solution at 25° C. and rubbed with a finger, it was checked (observed) that a slippery and lower frictional surface was formed, as compared with an untreated tube.

In addition, tetrabutylammonium bromide remaining in the coated tube (8) was quantified by LC-MS measurement. As a result, an amount of tetrabutylammonium bromide remaining in the coated tube (8) was as small as 5 µg/cm$^2$ per unit area. Conditions for the LC-MS measurement were as described in the above section "Washing step (II)."

Example 9

A coated tube (9) was produced in the same manner as in Example 6 except that tetrabutylammonium iodide (Tokyo Chemical Industry Co., Ltd.) was used instead of tetrabutylammonium fluoride.

A surface analysis of the coated tube (9) was performed by ATR-IR, a peak of the epoxy group became small, and the reaction of the epoxy group was checked (observed). In addition, no peak of tetrabutylammonium iodide was checked (observed).

When the coated tube (9) was immersed in a physiological salt solution at 25° C. and rubbed with a finger, it was checked (observed) that a slippery and lower frictional surface was formed, as compared with an untreated tube.

Example 10

A coated tube (10) was produced in the same manner as in Example 6 except that tetrabutylammonium hydrogen sulfate (Tokyo Chemical Industry Co., Ltd.) was used instead of tetrabutylammonium fluoride.

A surface analysis of the coated tube (10) was performed by ATR-IR, a peak of the epoxy group became small, and the reaction of the epoxy group was checked (observed). In addition, no peak of tetrabutylammonium hydrogen sulfate was checked (observed).

When the coated tube (10) was immersed in a physiological salt solution at 25° C. and rubbed with a finger, it was checked (observed) that a slippery and lower frictional surface was formed, as compared with an untreated tube.

Example 11

A coated tube (11) was produced in the same manner as in Example 6 except that tetrabutylammonium perchlorate (Tokyo Chemical Industry Co., Ltd.) was used instead of tetrabutylammonium fluoride.

A surface analysis of the coated tube (11) was performed by ATR-IR, a peak of the epoxy group became small, and the reaction of the epoxy group was checked (observed). In addition, no peak of tetrabutylammonium perchlorate was checked (observed).

When the coated tube (11) was immersed in a physiological salt solution at 25° C. and rubbed with a finger, it was checked (observed) that a slippery and lower frictional surface was formed, as compared with an untreated tube.

Example 12

A coated tube (12) was produced in the same manner as in Example 6 except that tetrabutylammonium hydroxide (a 10% isopropyl alcohol solution, Tokyo Chemical Industry Co., Ltd.) was used instead of tetrabutylammonium fluoride, and an addition amount thereof was changed to 0.05 times the amount (mass ratio) of the block copolymer (1).

A surface analysis of the coated tube (12) was performed by ATR-IR, a peak of the epoxy group became small, and the reaction of the epoxy group was checked (observed). In addition, no peak of tetrabutylammonium hydroxide was checked (observed).

When the coated tube (12) was immersed in a physiological salt solution at 25° C. and rubbed with a finger, it was checked (observed) that a slippery and lower frictional surface was formed, as compared with an untreated tube.

Example 13

The block copolymer (1) obtained in Synthesis Example 1 was dissolved in acetone such that a concentration became 6% by mass, and tetrabutylammonium bromide (Tokyo Chemical Industry Co., Ltd.) was added by an amount (mass ratio) 1.5 times the amount of the block copolymer (1) and dissolved, and thereby a mixed solution was prepared. A tube made of a polyamide elastomer (VESTAMID (registered trademark) E62-S1 manufactured by Daicel-Evonik Ltd.) having an outer diameter of 5 Fr (1.65 mm diameter) was immersed in the above mixed solution, dried at room temperature (25° C.) for 1 hour to form a coating film. In addition, the tube was stored at room temperature (25° C.) for 24 hours and then was immersed in water at room temperature for 10 minutes, and thereby tetrabutylammonium bromide was eluted and removed from the coating film. The tube was dried at room temperature to produce a coated tube (13) having a coating layer (lubricating layer) containing a cross-linked copolymer derived from the block copolymer (1) on the surface.

A surface analysis of the coated tube (13) was performed by ATR-IR, a peak of the epoxy group became small, and the reaction of the epoxy group was checked (observed). In addition, no peak of tetrabutylammonium bromide was checked (observed).

When the coated tube (13) was immersed in a physiological salt solution at 25° C. and rubbed with a finger, it was checked (observed) that a slippery and lower frictional surface was formed, as compared with an untreated tube.

Example 14

A coated tube (14) was produced in the same manner as in Example 13 except that a mixed solution containing the block copolymer (1) and the like was applied and dried, and then the tube was stored in an oven at 50° C. for 3 hours to heat the coating film.

A surface analysis of this coated tube was performed by ATR-IR, a peak of the epoxy group became small, and the reaction of the epoxy group was checked (observed). In addition, no peak of tetrabutylammonium bromide was checked (observed).

When the coated tube (14) was immersed in a physiological salt solution at 25° C. and rubbed with a finger, it was checked (observed) that a slippery and lower frictional surface was formed, as compared with an untreated tube.

Example 15

A coated wire (1) was produced in the same manner as in Example 3 except that a mixed solution containing the block copolymer (1) and the like was prepared in the same manner as in Example 3, and a target to which the mixed solution is applied was changed to a SUS314 wire having an outer diameter of 5 Fr (a diameter of 1.65 mm).

A surface analysis of the coated wire (1) was performed by ATR-IR, a peak of the epoxy group became small, and the reaction of the epoxy group was checked (observed). In addition, no peak of tetrabutylammonium bromide was checked (observed).

When the coated wire (1) was immersed in a physiological salt solution at 25° C. and rubbed with a finger, it was checked (observed) that a slippery and lower frictional surface was formed, as compared with an untreated wire.

Example 16

A coated wire (2) was produced in the same manner as in Example 15 except that a mixed solution containing the block copolymer (1) and the like was applied and dried, and then the wire was stored in an oven at 130° C. for 1 hour to heat the coating film.

A surface analysis of the coated wire (2) was performed by ATR-IR, a peak of the epoxy group became small, and the reaction of the epoxy group was checked (observed). In addition, no peak of tetrabutylammonium bromide was checked (observed).

When the coated wire (2) was immersed in a physiological salt solution at 25° C. and rubbed with a finger, it was checked (observed) that a slippery and lower frictional surface was formed, as compared with an untreated wire.

Comparative Example 1

The block copolymer (1) obtained in Synthesis Example 1 was dissolved in N,N-dimethylformamide (DMF) such that a concentration became 6% by mass, and tetramethylammonium bromide (Tokyo Chemical Industry Co., Ltd.) was added by an amount (mass ratio) 0.5 times the amount of the block copolymer (1). However, tetramethylammonium bromide was not dissolved, and a mixed solution could not be prepared.

Comparative Example 2

A comparative coated tube (1) was produced in the same manner as in Example 1 except that tetraoctylammonium bromide (Wako Pure Chemical Industries, Ltd.) was used instead of tetraethylammonium bromide.

A surface analysis of the comparative coated tube (1) was performed by ATR-IR, a peak of the epoxy group became small, and the reaction of the epoxy group was checked (observed). In addition, a peak of tetraoctylammonium bromide was observed, and it was confirmed that the ammonium salts were not removed.

When the comparative coated tube (1) was immersed in a physiological salt solution at 25° C. and rubbed with a finger, a surface was not slippery and did not had lower friction as compared with an untreated tube.

Comparative Example 3

A comparative coated tube (2) was produced in the same manner as in Example 6 except that the alkylammonium salts were not added when preparing the mixed solution containing the block copolymer (1) obtained in Synthesis Example 1.

When the comparative coated tube (2) was immersed in a physiological salt solution at 25° C. and rubbed with a finger, it was checked (observed) that a slippery and lower frictional surface as compared with an untreated tube was formed.

Comparative Example 4

A comparative coated wire (1) was produced in the same manner as in Example 16 except that the alkylammonium salts were not added when preparing the mixed solution containing the block copolymer (1) obtained in Synthesis Example 1.

Comparative Example 5

A comparative coated tube (3) was produced in the same manner as in Example 6 except that a mixed solution prepared using pyridine (Tokyo Chemical Industry Co., Ltd.) instead of tetrabutylammonium fluoride was applied and dried, and then the tube was stored in an oven at 80° C. for 18 hours to heat the coating film.

When the comparative coated tube (3) was immersed in a physiological salt solution at 25° C. and rubbed with a finger, it was checked (observed) that a slippery and lower frictional surface as compared with an untreated tube was formed.

Evaluation of Sliding Durability

The sliding durability (i.e., the durability of the lubricating layer) of the coated tubes and wires and the comparative coated tubes and wires, obtained in Examples 1 to 16 and Comparative Examples 2 to 5 (hereinafter, also simply referred to as "samples"), was evaluated according to the following method.

Evaluation Method

Each sample was immersed in distilled water, and slidability was organoleptically evaluated by a method of sandwiching the sample by hand and rubbing it in a longitudinal direction. The sliding durability was evaluated by measuring the number of times of rubbing until the lubricity (smoothness) was impaired. It was determined that the greater the number of times of rubbing, the better the sliding durability.

The results are shown in Table 1 below. In addition, regarding the item of "sliding durability" in the table, "-" indicates that the sliding durability could not be evaluated. Furthermore, ">20" indicates that the slidability was not impaired even when the sample was rubbed at least 20 times.

ammonium salt is a halide ion. In particular, the sliding durability was particularly improved when an anion of the ammonium salt was a chloride ion or a bromide ion (Examples 7 and 8). Sliding durability was also improved when an anion of the ammonium salt was an iodide ion (Example 9).

Furthermore, favorable sliding durability was obtained even at a low treatment temperature as in Examples 13 and 14. This results from a reaction of glycidyl groups in the copolymer proceeded sufficiently by addition of the specific ammonium salt.

REFERENCE SIGNS LIST 10 medical instrument
1 base layer
1a core part of base layer
1b base surface layer
2 lubricating layer

What is claimed is:

1. A method for producing a medical instrument having a lubricating layer that exhibits lubricity, the method comprising:

applying a solution, to a base layer of the medical instrument, the solution containing a block copolymer having a structural unit (A) derived from a reactive monomer having an epoxy group and a structural unit

TABLE 1

| | Base | Ammonium salt Type | Carbon number of cation | Mass ratio (to copolymer (1)) | Solvent for mixed solution | Condition of drying or heat treatment | Sliding durability |
|---|---|---|---|---|---|---|---|
| Example 1 | PA elastomer | Et$_4$NBr | 8 | 0.5 | DMF | 80° C. × 5 hr | >20 |
| Example 2 | PA elastomer | n-Pr$_4$NBr | 12 | 0.5 | DMF | 80° C. × 5 hr | >20 |
| Example 3 | PA elastomer | n-Bu$_4$NBr | 16 | 0.5 | DMF | 80° C. × 5 hr | >50 |
| Example 4 | PA elastomer | n-Pentyl$_4$NBr | 20 | 0.5 | DMF | 80° C. × 5 hr | >50 |
| Example 5 | PA elastomer | n-Hexyl$_4$NBr | 24 | 0.5 | DMF | 80° C. × 5 hr | >20 |
| Example 6 | Polyethylene | n-Bu$_4$NF | 16 | 0.5 | DMF | 80° C. × 5 hr | >30 |
| Example 7 | Polyethylene | n-Bu$_4$NCl | 16 | 0.5 | DMF | 80° C. × 5 hr | >50 |
| Example 8 | Polyethylene | n-Bu$_4$NBr | 16 | 0.5 | DMF | 80° C. × 5 hr | >50 |
| Example 9 | Polyethylene | n-Bu$_4$NI | 16 | 0.5 | DMF | 80° C. × 5 hr | >40 |
| Example 10 | Polyethylene | n-Bu$_4$NHSO$_4$ | 16 | 0.5 | DMF | 80° C. × 5 hr | >20 |
| Example 11 | Polyethylene | n-Bu$_4$NClO$_4$ | 16 | 0.5 | DMF | 80° C. × 5 hr | >20 |
| Example 12 | Polyethylene | n-Bu$_4$NOH | 16 | 0.05 | DMF | 80° C. × 5 hr | >20 |
| Example 13 | PA elastomer | n-Bu$_4$NBr | 16 | 1.5 | Acetone | 25° C. × 24 hr | >50 |
| Example 14 | PA elastomer | n-Bu$_4$NBr | 16 | 1.5 | Acetone | 50° C. × 3 hr | >50 |
| Example 15 | SUS | n-Bu$_4$NBr | 16 | 0.5 | DMF | 80° C. × 5 hr | >50 |
| Example 16 | SUS | n-Bu$_4$NBr | 16 | 0.5 | DMF | 130° C. × 1 hr | >50 |
| Comparative Example 1 | — | Me$_4$NBr | 4 | 0.5 | DMF | — | — |
| Comparative Example 2 | PA elastomer | n-Octyl$_4$NBr | 32 | 0.5 | DMF | 80° C. × 5 hr | — |
| Comparative Example 3 | Polyethylene | Not used | — | — | DMF | 80° C. × 5 hr | 3 |
| Comparative Example 4 | SUS | Not used | — | — | DMF | 130° C. × 1 hr | 5 |
| Comparative Example 5 | Polyethylene | (Pyridine) | — | (0.5) | DMF | 80° C. × 18 hr | 5 |

As evidenced by the results set forth in Table 1, it was shown that a medical instrument having a lubricating layer having excellent sliding durability can be obtained by using a mixed solution containing a specific ammonium salt. In particular, comparison with Examples 1 to 5 revealed that use of an ammonium salt having 16 to 20 carbon atoms particularly improved the slidability. In addition, from the comparison of Examples 6 to 12, it can be said that the sliding durability is easily improved when an anion of the (B) derived from a hydrophilic monomer, an alkylammonium salt having 8 to 24 carbon atoms, and a solvent; and washing the medical instrument following the applying of the solution to the base layer to remove the alkylammonium salt and improve the lubricity of the lubricating layer on the medical instrument.

2. The method for producing a medical instrument according to claim 1, wherein the solution is maintained at 110° C. or lower after the applying of the solution to the base layer.

3. The method for producing a medical instrument according to claim 1, wherein the alkylammonium salt is a tetraalkylammonium salt.

4. The method for producing a medical instrument according to claim 1, wherein the alkylammonium salt is selected from the group consisting of a tetraethylammonium salt, a tetra-n-propylammonium salt, a tetra-n-butylammonium salt, a tetra-n-pentylammonium salt, and a tetra-n-hexylammonium salt.

5. The method for producing a medical instrument according to claim 1, wherein the alkylammonium salt is an anion of the alkylammonium salt selected from the group consisting of a halide ion, a hydrogen sulfate ion, a perchlorate ion, and a hydroxide ion.

6. The method for producing a medical instrument according to claim 5, wherein the anion of the alkylammonium salt is a halide ion.

7. The method for producing a medical instrument according to claim 1, wherein the alkylammonium salt has 16 to 20 carbon atoms.

8. The method for producing a medical instrument according to claim 1, wherein the reactive monomer having an epoxy group is at least one selected from the group consisting of glycidyl acrylate, glycidyl methacrylate, 3,4-epoxycyclohexylmethyl acrylate, 3,4-epoxycyclohexylmethyl methacrylate, 13-methylglycidyl methacrylate, and allyl glycidyl ether.

9. The method for producing a medical instrument according to claim 1, wherein the hydrophilic monomer is at least one selected from the group consisting of acrylamide and derivatives thereof, vinylpyrrolidone and derivatives thereof, acrylic acid and derivatives thereof, methacrylic acid and derivatives thereof, polyethylene glycol acrylate and derivatives thereof, monomers having sugars and phospholipids in their side chains and derivatives thereof, and water-soluble monomers and derivatives thereof.

10. The method for producing a medical instrument according to claim 1, wherein the hydrophilic monomer is at least one selected from the group consisting of N,N-dimethylacrylamide, acrylamide, 2-hydroxyethyl methacrylate, and N-vinylpyrrolidone.

11. The method for producing a medical instrument according to claim 1, wherein the solution contains 1% to 10% by mass of the block copolymer.

12. The method for producing a medical instrument according to claim 1, wherein the solution contains the block copolymer and the alkylammonium salt at a mass ratio of 1:0.05 to 1:2.

13. The method for producing a medical instrument according to claim 1, further comprising:
(I') subjecting the medical instrument to drying and/or heat treating after the applying of the solution to the base layer.

14. The method for producing a medical instrument according to claim 13, wherein the medical instrument is dried at a temperature of 10° C. to 30° C. for 30 minutes to 5 hours.

15. The method for producing a medical instrument according to claim 13, wherein the medical instrument is heat treated at a temperature of 40° C. to 200° C. for 1 to 10 hours.

16. The method for producing a medical instrument according to claim 13, wherein the base layer to which the solution is applied is dried at a temperature of 10° C. to 30° C. for 5 to 30 hours.

17. The method for producing a medical instrument according to claim 1, wherein the molar ratio of the structural unit (A) to the structural unit (B) is 1:2 to 1:100.

18. The method for producing a medical instrument according to claim 1, wherein the solvent is selected from the group consisting of water, methanol, ethanol, isopropanol, ethylene glycol, acetone, methyl ethyl ketone, cyclohexanone, ethyl acetate, chloroform, hexane, tetrahydrofuran (THF), butyl ether, benzene, toluene, N,N-dimethylformamide (DMF), dimethyl sulfoxide and combinations thereof.

19. The method for producing a medical instrument according to claim 1, the solution further comprising at least one pharmaceutical active ingredient, the at least one pharmaceutical active ingredient being one of: an anticancer drug, an immunosuppressant, an antibiotic, an antirheumatic drug, an antithrombotic drugs, a HMG-CoA reductase inhibitor, an ACE inhibitors, a calcium antagonist, an antihyperlipidemic agent, an integrin inhibitor, an antiallergic agent, an antioxidant, a GPIIb/IIIa antagonist, a retinoid, a flavonoid, a carotenoid, a lipid improver, a DNA synthesis inhibitor, a tyrosine kinase inhibitor, an antiplatelet drug, a vascular smooth muscle growth inhibitor, an anti-inflammatory drug, a biological material, interferon, and a NO production promoting substance.

20. The method for producing a medical instrument according to claim 1, wherein the medical instrument is a catheter configured to be positioned in a living body, a guide wire configured to be positioned in a living body, or a needle configured to be positioned in a living body.

* * * * *